United States Patent [19]

Pilgram et al.

[11] Patent Number: 4,558,040

[45] Date of Patent: Dec. 10, 1985

[54] MITICIDAL (2-ALKYL-3,4-DIHYDRO-2H-1-BENZOPYRAN-8-YL)-DIAZENECARBOXYLIC ACID ESTERS

[75] Inventors: Kurt H. Pilgram; Richard D. Skiles, both of Modesto, Calif.

[73] Assignee: Shell Oil Company, Houston, Tex.

[21] Appl. No.: 677,403

[22] Filed: Dec. 3, 1984

[51] Int. Cl.[4] .................... A61N 59/10; C09B 29/22

[52] U.S. Cl. ..................................... 514/150; 534/617; 534/787; 549/404; 568/584; 568/588; 568/706; 568/709

[58] Field of Search ................ 549/404; 534/617, 787; 514/150

[56] References Cited

U.S. PATENT DOCUMENTS 4,169,097  9/1979  Wright et al. ...................... 549/404

Primary Examiner—Nicky Chan

[57] ABSTRACT

Certain miticidal (2-alkyl-3,4-dihydro-2H-1-benzopyran-8-yl)diazenecarboxylic acid esters.

3 Claims, No Drawings

MITICIDAL (2-ALKYL-3,4-DIHYDRO-2H-1-BENZOPYRAN-8-YL)-DIAZENECARBOXYLIC ACID ESTERS

DESCRIPTION OF THE INVENTION

It has been found that certain (2-alkyl-3,4-dihydro-2H-1-benzopyran-8-yl)diazenecarboxylic acid esters are toxic with respect to mites that feed upon plants.

These miticides are described by the generic formula:

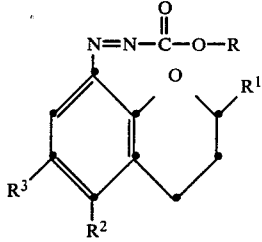
(I)

wherein R contains up to three carbon atoms and is alkyl or alkenyl; $R^1$ is alkyl of one to three carbon atoms; $R^2$ and $R^3$ each is bromine, chlorine or alkyl of one to three carbon atoms, with the proviso that at least one of $R^2$ and $R^3$ is not hydrogen.

In these compounds, each alkyl moiety suitably is straight-chain or branched-chain.

Because of their activity with respect to mites, the species of the subgenus wherein R and $R^1$ each is methyl are preferred. For the same reason it is preferred that when any of $R^2$ and $R^3$ is alkyl, it is methyl, and chlorine is the preferred halogen.

Compounds of Formula I can be prepared by treating the corresponding 2-(2-alkyl-3,4-dihydro-2H-1-benzopyran-8-yl)hydrazinecarboxylic acid ester with meta-chloroperoxybenzoic acid (MCPBA) in the presence of an inert solvent, such as methylene chloride. The treatment is effectively conducted by adding a solution of the MCPBA in the solvent to a stirred solution of the ester in the solvent at room temperature, then warming and stirring the resulting mixture at a temperature of about 30°–50° C. for a sufficient time for the reaction to go to completion. In some cases, it may be found desirable to mix the reactants at a lower temperature—for example about 0°–10° C.—then warming the mixture. The reaction proceeds according to the equation:

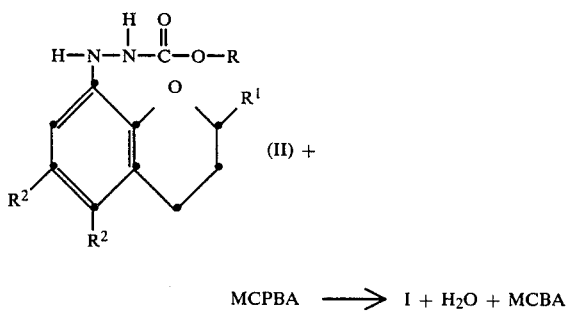

MCPBA ⟶ I + H₂O + MCBA

Compounds of Formula II can be prepared by treating the appropriate 8-hydrazino-3,4-dihydrobenzopyran with the appropriate R-ester of chloroformic acid in the presence of a tertiary amine as hydrogen chloride acceptor. The reaction proceeds according to the equation:

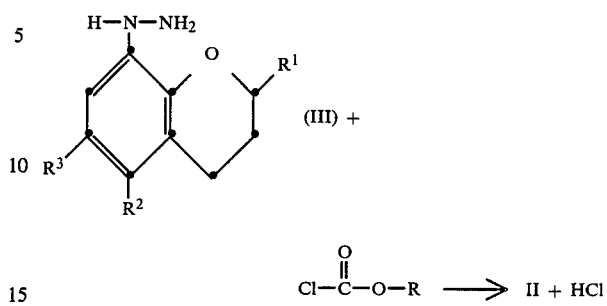

$$Cl-\overset{O}{\underset{\|}{C}}-O-R \longrightarrow II + HCl$$

This reaction can be effected by slowly adding one of the reagents to a stirred solution of the other reagent in an inert solvent (tetrahydrofuran (THF) is a typical example) in the presence of the amine at a low temperature—for example −5° C. to 0° C.—then if necessary warming the mixture or even heating it at reflux temperature for a time sufficient to ensure completion of the reaction. The Formula II species is isolated from the reaction mixture, and purified, by conventional means, as is shown in particular instances in the Examples, hereinafter. The R-esters of chloroformic acid are known and readily available materials. A suitable hydrogen chloride acceptor in many instances is N,N-diisopropyl-N-ethylamine; triethylamine and pyridine are also suitable.

The 8-hydrazino-3,4-dihydrobenzopyrans (III) are prepared from the corresponding 8-nitro-3,4-dihydrobenzopyrans (IV) according to the reactions expressed by the equations

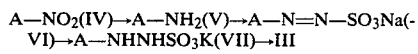
A—NO₂(IV)→A—NH₂(V)→A—N=N—SO₃Na(-VI)→A—NHNHSO₃K(VII)→III wherein A represents

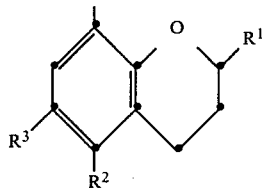

Intermediate V is prepared by conventional Raney nickel-catalyzed hydrogenation in a Parr shaker of a solution of intermediate IV in an inert solvent such as THF. Intermediate VI is prepared by diazotizing intermediate V, followed by treatment with sodium sulfite. The diazotization is conventional, effected by treating IV with concentrated hydrochloric acid at about room temperature, diluting the mixture with water, cooling it to about 0° C. and slowly adding an aqueous solution of sodium nitrite to the stirred mixture. Then the diazonium salt solution is added to a cold aqueous solution/-suspension of sodium sulfite, and the mixture is stirred at room temperature to complete the reaction. Intermediate VI may be isolated and further treated, or the crude product may be used to prepare intermediate VII. In either case, aqueous VI is treated with sodium dithionite (added in portions to the stirred mixture at room temperature), then potassium chloride is added and the mixture is stirred at a moderately elevated temperature (for example, 60°-80° C.) for a time sufficient to complete the reaction. Intermediate VII is recovered as a solid by filtering the mixture. VII then can be converted to intermediate III by mixing it with a lower alkanol, such as methanol, treating the cold (0° C.) mixture with hydrogen chloride, evaporating the alkanol, treating the residue with aqueous sodium hydroxide, and extracting the resulting III, using a suitable solvent.

The 8-nitro-3,4-dihydrobenzopyran precursors (IV) can be prepared according to the reactions expressed by the equations:

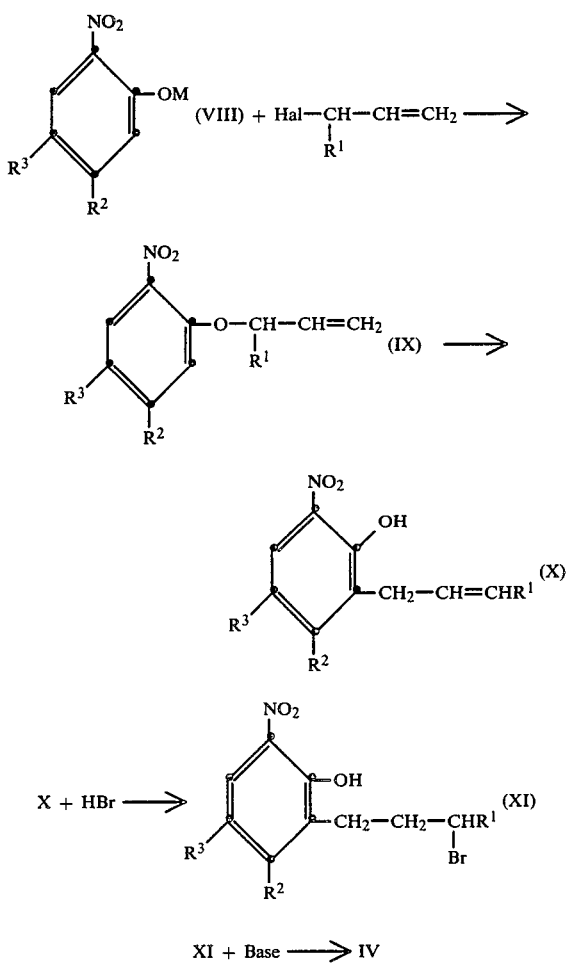

XI + Base ⟶ IV

The 2-(2-alkenyloxy)-6-nitrophenol precursors (X) can be prepared from the appropriate 2-nitrophenol by the general procedures described in U.S. Pat. Nos. 3,412,110 and 4,406,910 for the preparation of 2,3-dihydrobenzofurans: an alkali metal (M) salt of the phenol (VIII) is treated with the appropriate 3-halo-1-alkene, and the resulting 1-(2-alkenyloxy)-2-nitrobenzene (IX) is Claisen-rearranged to form the corresponding 2-(2-alkenyl)-6-nitrophenol (X).

Conversion of VIII to IX can be effected by treating a solution of the phenol VIII, in a solvent such as DMSO, with an alkali metal base such as sodium hydroxide or sodium hydride, in the presence of, or subsequently treating the alkali metal phenoxide thus formed with, the appropriate alkenyl halide, then heating the resulting mixture at a moderately elevated temperature, for example, 80°-120° C.

Claisen-rearrangement of IX is effected conventionally—conveniently by heating IX to a moderately elevated temperature—e.g., 150°-250° C.—in an inert atmosphere.

Conversion of X to XI is effected by treating a solution of X in an inert solvent, such as glacial acetic acid, with a strong aqueous solution of hydrogen bromide at a moderately elevated temperature, conveniently the reflux temperature of the reaction mixture.

Cyclization of XI to form IV is effected by treating a solution of XI in an inert solvent, such as DMSO, with a strong base, such as sodium hydride.

The preparation, isolation and physical properties of typical individual species of the compounds of Formula I, in particular instances, are described in the following examples. The identity of each product, and each of the intermediates involved, was confirmed by appropriate chemical and spectral analyses.

EXAMPLE 1

(3,4-Dihydro-2,5-dimethyl-2H-1-benzopyran-8-yl)diazenecarboxylic acid methyl ester (1)

24 g of sodium hydride was added in portions to a stirred mixture of 153 g of 5-methyl-2-nitrophenol and 500 ml of DMSO. Then 135.7 g of 3-chloro-1-butene was added drop-by-drop (over 5 minutes) to the stirred mixture, which then was stirred at reflux (79°-81° C.) for 24 hours. Then the mixture was made basic with 50% aqueous sodium hydroxide, poured over ice water and extracted with methylene chloride. The extract was washed with cold water, dried (MgSO₄), filtered and stripped of solvent, to give 1-(1-methyl-2-propenyloxy)-5-methyl-2-nitrobenzene (1A), as a dark-colored syrup.

197 g of 1A was placed in a flask, which then was purged with nitrogen, and a slow stream of nitrogen was passed through the system while the 1A was heated gradually. At about 160° C., an exothermic reaction began, and the temperature rose to 220° C. The mixture was contained with cooling, then heated at 185°-200° C. for 1.5 hours, diluted with ether, and filtered. The solvent was evaporated from the filtrate to give crude 2-(1-methyl-2-propenyl)-3-methyl-6-nitrophenol (1B), as a dark syrup.

A mixture of 155 ml of the crude 1B, 15 ml of glacial acetic acid and 135 ml of 48% hydrobromic acid was stirred at reflux (113° C.) for five hours, then concentrated at 30 Torr. and 80° C. for one hour. The residue was taken up in 500 ml of ether, dried (MgSO₄), and filtered through Celite, and the solvent was evaporated from the filtrate. The residue was column-chromatographed on silica gel, using a 1:24 v:v mixture of THF and hexane as eluent. The product was recrystallized from ether/hexane to give 2-(3-bromobutyl)-3-methyl-6-nitrophenol (1C), as a light yellow solid, m.p.: 67°-69° C.

40.5 g of 1C was added in portions over 20 minutes to a stirred mixture of 3.4 g of sodium hydride in 300 ml of DMSO at room temperature, and the resulting mixture was stirred for 18 hours at room temperature. The mixture was poured into ice water, made slightly acidic with concentrated hydrochloric acid and filtered. The solid was dried to give 3,4-dihydro-2,5-dimethyl-8-nitro-2H-1-benzopyran (1D) as a yellow solid, m.p.: 83°-85° C.

A mixture of 27 g of 1D, 200 ml of THF and 2 g of activated Raney nickel catalyst was treated with hydrogen (40 psig) in a Parr shaker for 3 hours. The resulting mixture was dried (MgSO$_4$), filtered and concentrated to dryness, to give 8-amino-3,4-dihydro-2,5-dimethyl-2H-1-benzopyran (1E), as an amber syrup.

23 g of 1E was mixed with 60 ml of concentrated hydrochloric acid and the mixture was warmed to 70° C., then stirred to room temperature. Then the mixture was cooled to 0° C. and 120 g of ice water was added, followed by addition, drop-by-drop over 15 minutes, of a solution of 9.9 g of sodium nitrite in 30 ml of water. The resulting mixture was stirred at 0° C. for 30 minutes, poured into a cold (0° C.) mixture of 120 g of sodium sulfite in 450 ml of water, and stirred at room temperature for three hours. Then 22.6 g of sodium dithionite was added in portions to the stirred mixture, at room temperature and the mixture was stirred at room temperature for 18 hours. The stirred mixture was heated to 75° C., 125 g of potassium chloride was added, the mixture was stirred at 75° C. for 15 minutes and then chilled to 0° C. and filtered. The solid was dried and mixed with 300 ml of methanol. The resulting slurry was stirred and cooled to −10° C. while excess anhydrous hydrogen chloride was added. The resulting mixture was stirred to 5° C., the methanol was evaporated therefrom, and the residue was taken up in 300 ml of water. The resulting mixture was made basic with 50% aqueous sodium hydroxide, and extracted with ether. The extract was dried (MgSO$_4$), filtered and concentrated to dryness at 25° C. and 30 Torr, to give 8-hydrazino-3,4-dihydro-2,5-dimethyl-2H-1-benzopyran (1F), as an amber syrup.

A stirred mixture of the 1F, 200 ml of THF and 12.4 g of N,N-diisopropyl-N-ethylamine was chilled to 0° C. and 9.1 g of methyl chloroformate was added, drop-by-drop, over five minutes. The mixture was poured over ice water and extracted with ether. The extract was dried (MgSO$_4$) and concentrated to dryness, to give the methyl ester of 2-(3,4-dihydro-2,5-dimethyl-2H-1-benzopyran-8-yl)hydrazinecarboxylic acid (1G), as an amber syrup.

A solution of 13.8 g of MCPBA in 100 ml of methylene chloride was added drop-by-drop over 10 minutes to a stirred solution of 16.1 g of 1G in 150 ml of methylene chloride at room temperature. The resulting mixture was stirred and refluxed (35° C.) for 30 minutes, then washed with 10% aqueous sodium carbonate solution. The resulting methylene chloride solution was dried (MgSO$_4$), and the solvent was evaporated. The residue was purified by column chromatography over silica gel, using a 1:4:20 v:v:v mixture of THF, ethyl acetate and hexane as eluent, to give 1, as a brick red solid, m.p.: 95°–97° C.

EXAMPLES 2 and 3

The ethyl ester (2) and the allyl ester (3) of (3,4-dihydro-2,5-dimethyl-2H-1-benzopyran-8-yl)diazenecarboxylic acid were prepared as orange syrups, from ethyl and allyl chloroformates, respectively, by the procedures described in Example 1 for preparing 1 from methyl chloroformate.

EXAMPLE 4

(5-chloro-3,4-dihydro-2,6-dimethyl-2H-1-benzopyran-8-yl)diazenecarboxylic acid methyl ester (4)

1.3 liters of concentrated sulfuric acid was added to a stirred mixture of 566 g of 3-chloro-4-methylaniline and 3 liters of water. The mixture warmed to 104° C. The mixture was cooled to 10°–15° C. and stirred while a solution of 290 g sodium nitrite in 1 liter of water was added drop-by-drop (over 2 hours). The mixture was stirred for 1 hour at about 10° C., then was added drop-by-drop (over 2 hours) to a stirred solution of 1 liter of concentrated sulfuric acid in 1.5 liters of water, at 110°–115° C. The resulting mixture was stirred at reflux temperature for one hour, cooled to room temperature and extracted with ether. The extract (4 liters) was mixed with 4 liters of water. The resulting mixture was stirred at 15° C. while 700 ml of a 50% aqueous solution of sodium hydroxide was slowly added (over 1 hour). The aqueous phase was separated, cooled to 15°–20° C. and stirred while 1.3 liters of concentrated hydrochloric acid was added. The resulting mixture was extracted with ether, the extract was dried (MgSO$_4$) and the solvent was evaporated to give 3-chloro-4-methylphenol (4A), as an amber oil.

247 g of 90% aqueous nitric acid was added drop-by-drop (over 2.5 hours) to a stirred mixture of 503.5 g of 4A and 2 liters of glacial acetic acid, at 5°–10° C. The resulting mixture was stirred at 10°–15° C. for 2 hours, and poured over 5 liters of ice water. The resulting mixture was stirred for 18 hours at room temperature, then extracted with a 2:3 v:v mixture of ether and hexane. The extract was washed with cold water, dried, and the solvents were evaporated. The residue was dissolved in 2 liters of ether, the solution was cooled to −60° C., held at that temperature for 30 minutes and filtered. The collected solid was washed with a cold (−60° C.) 1:1 v:v mixture of ether and hexane and air-dried to give 3-chloro-4-methyl-6-nitrophenol (4B), as a yellow solid, m.p.: 70°–71° C.

4 was prepared, as an orange solid, m.p.: 90°–92° C., from 4B by the procedures described in Example 1 for preparing 1 from 5-methyl-2-nitrophenol.

EXAMPLE 5

The ethyl ester of (5-chloro-3,4-dihydro-2,6-dimethyl-2H-1-benzopyran-8-yl)diazenecarboxylic acid (5) was prepared, as an orange solid, m.p.: 90°–92° C., from ethyl chloroformate by the procedures described for the preparation of 4 from methyl chloroformate.

Compounds of Formula I have been found to be toxic to mites that feed on plants, with little or no toxicity to other pests which feed on plants.

Accordingly, the invention includes a method for combatting plant-feeding mites which comprises applying to the foliage of the plants to be protected an effective amount of a compound of Formula I.

For application, the compound of the invention ordinarily is applied most effectively by formulating it with a suitable inert carrier or surface-active agent, or both. The invention, therefore, also includes compositions suitable for combatting mites, such compositions comprising an inert carrier or surface-active agent, or both, and as active ingredient at least one compound of the invention.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25-75% by weight of active compound and usually contain, in addition to the solid carrier, 3-10% by weight of a dispersing agent, 2-15% of a surface-active agent and, where necessary, 0-10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5-10% by weight of the active compound. Granules are usually prepared to have a size between 10 and 100 BS mesh (1.676-0.152 mm), and may be manufactured by agglomeration or impregnation techniques. Generally, granules will contain 0.5-25% by weight of the active compound, 0-1% by weight of additives such as stabilizers, slow release modifiers and binding agents. Emulsifiable concentrates usually contain, in addition to the solvent and, when necessary, cosolvent, 10-50% weight per volume of the active compound, 2-20% weight per volume emulsifiers and 0-20% weight per volume of appropriate additives such as stabilizers, penetrants and corrosion inhibitors. Suspension concentrates are compounded so as to obtain a stable, non-sedimenting, flowable product and usually contain 10-75% weight of the active compound, 0.5-5% weight of dispersing agents, 1-5% of surface-active agent, 0.1-10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Of particular interest in current practice are the water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or more by weight of finely divided active material, 3-7% by weight of a blend of surfactants, which act as wetting, dispersing, suspending and binding agents, and 1-3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.0001% by weight to as much as about 95% by weight of a compound of the invention as the active ingredient.

The compositions of the invention may also contain other ingredients, for example, other compounds possessing pesticidal, especially insecticidal, acaricidal or fungicidal properties, as are appropriate to the intended purpose.

The method of applying a compound of the invention to control mites comprises applying the compound, ordinarily in a composition of one of the aforementioned types, to a locus or area to be protected from the mites, such as the foliage and/or the fruit of plants. The compound, of course, is applied in an amount sufficient to effect the desired action. This dosage is dependent upon many factors, including the carrier employed, the method and conditions of the application, whether the formulation is present at the locus in the form of an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of the invention at the locus to be protected—i.e., the dosage which the mite contacts—is of the order of 0.001 to 0.5% based on the total weight of the formulation, though under some circumstances the effective concentration will be as little as 0.0001% or as much as 2%, on the same basis.

Miticidal Activity

Toxicity of compounds of this invention with respect to mites was determined as follows:

Adult female two-spotted spider mites (*Tetranychus urticae* (Koch)) were tested by placing 50–75 mites on the bottom side of leaves of pinto bean plants. The leaves were sprayed with dilutions of acetone solution of test compound into water containing an emulsifier and kept under laboratory conditions for about 20 hours at which time mortality counts were made. The tests were conducted employing several different dosage rates of test compounds.

In each set of tests, identical tests were conducted using Parathion as a standard for comparison.

In each instance, the toxicity of the test compound was compared to that of the standard pesticide (Parathion), its relative toxicity then being expressed in terms of the relationship between the amount of the test compound and the amount of the standard pesticide required to produce the same percentage (50%) of mortality in the mites. By assigning the standard pesticide an arbitrary rating of 100, the toxicities of the test compound was expressed in terms of the Toxicity Index, which compares the toxicity of the test compound of the invention with that of the standard pesticide. That is to say, a test compound having a Toxicity Index of 50 would be half as active, while one having a Toxicity Index of 200 would be twice as active, as the standard pesticide. The results are set forth in Table I.

TABLE I

| Compound Number | Toxicity Index, Two-Spotted Spider Mites |
|---|---|
| 1 | 470 |
| 2 | 260 |
| 3 | 330 |
| 4 | 400 |
| 5 | 520 |

In similar standardized tests, compounds of Formula I were found to have little or no toxicity with respect to houseflies, pea aphids, and corn earworms.

We claim:

1. A compound of the Formula

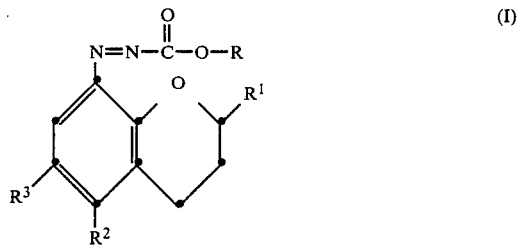

wherein R contains from one to three carbon atoms and is alkyl or alkenyl; $R^1$ is alkyl of one to three carbon atoms; $R^2$ and $R^3$ each is hydrogen, bromine, chlorine or alkyl of one to three carbon atoms, with the proviso that at least one of $R^2$ and $R^3$ is not hydrogen.

2. A compound according to claim 1 wherein R and $R^1$ each is methyl, and $R^2$ and $R^3$ each is hydrogen, methyl or chlorine.

3. A method for protecting a plant from mites which comprises applying to the plant a miticidally effective dosage of a compound of claim 1.

* * * * *